United States Patent [19]

Hatsuda et al.

[11] Patent Number: 5,140,076
[45] Date of Patent: Aug. 18, 1992

[54] METHOD OF TREATING THE SURFACE OF AN ABSORBENT RESIN

[75] Inventors: Takumi Hatsuda, Himeji; Kazumasa Kimura, Ikoma; Kinya Nagasuna; Akito Yano, both of Himeji, all of Japan

[73] Assignee: Nippon Shokubai Kagaku Kogyo Co., Ltd., Osaka, Japan

[21] Appl. No.: 502,738

[22] Filed: Apr. 2, 1990

[51] Int. Cl.$^5$ .................................................. C08F 2/16
[52] U.S. Cl. ........................................ 525/375; 526/62; 526/88; 526/317.1; 526/318.2
[58] Field of Search ............................ 525/375, 375.1; 526/318.2, 317.1, 88, 62

[56] References Cited

U.S. PATENT DOCUMENTS

| | | |
|---|---|---|
| 3,661,815 | 5/1972 | Smith . |
| 4,076,663 | 2/1978 | Masuda . |
| 4,301,266 | 11/1981 | Muenster et al. ............... 526/318.2 |
| 4,666,983 | 5/1987 | Tsubakimoto . |
| 4,734,478 | 3/1988 | Tsubakimoto . |

FOREIGN PATENT DOCUMENTS

| | | |
|---|---|---|
| 57-44627 | 3/1982 | Japan . |
| 58-42602 | 3/1983 | Japan . |
| 58-180233 | 10/1983 | Japan . |
| 59-62665 | 4/1984 | Japan . |
| 60-18690 | 5/1985 | Japan . |

OTHER PUBLICATIONS

Hawley's Condensed Chem. Dictionary, Van Nostrand Reinhold, N.Y., 1987, p. 944.

*Primary Examiner*—Joseph L. Schofer
*Assistant Examiner*—Tom Weber
*Attorney, Agent, or Firm*—Burns, Doane, Swecker & Mathis

[57] ABSTRACT

A method of treating the surface of an absorbent resin, which comprises mixing (A) 100 parts by weight of an absorbent resin powder possessing a carboxyl group (B) 0.01 to 30 parts by weight of a cross-linking agent, (C) 0 to 50 parts by weight of water, and (D) 0 to 60 parts by weight of a hydrophilic organic solvent in a high-speed stirring type mixer provided with an inner surface formed substantially of a substrate (I) possessing a contact angle of not less than about 60° with respect to water and a heat distortion point of not lower than about 70° C. and completing reaction of said absorbent resin powder (A) with said cross-linking agent (B).

30 Claims, 2 Drawing Sheets

METHOD OF TREATING THE SURFACE OF AN ABSORBENT RESIN

BACKGROUND OF THE INVENTION

1. Field of the Invention

The present invention relates to a method of treating the surface of an absorbent resin. More particularly, it relates to a method of treating the surface of the absorbent resin by crosslinking the surface region of the absorbent resin homogeneously and effectively using a crosslinking agent to obtain an absorbent which is excellent in absorption rate under pressure, water-retaining property under pressure and liquid permeability, and is suitable for use as a material in a sanitary article such as a sanitary napkin, a disposable diaper, etc.; as a water-retaining agent for agriculture and horticulture and aforestation; and as a material for other various absorbent articles.

2. Description of the Prior Art

Attempts have been made heretofore to use an absorbent resin as one of the component materials for such sanitary articles as sanitary napkins and disposable diapers which function to absorb body fluids. Absorbent resins of this nature heretofore known to the art include a hydrolyzed starch-acrylonitrile graft polymer (Japanese Patent Publication SHO 49(1974)-43,395), a neutralized starch-acrylic acid graft polymer (Japanese Patent Laid-Open SHO 51(1976)-125,468), a saponified vinyl acetate-acrylic ester copolymer (Japanese Patent Laid-Open SHO 52(1977)-14,689), a hydrolyzed acrylonitrile copolymer or acrylamide copolymer (Japanese Patent Publication SHO 53(1978)-15,959), cross-linked products thereof, a partially neutralized polyacrylic acid, and a partially neutralized cross-linked polyacrylic acid (Japanese Patent Laid-Open SHO 57(1982)-34,101).

Characteristic properties expected in absorbent resins include high absorption capacity, outstanding absorption rate and liquid permeability, and large gel strength. These characteristic properties, however, are not effected simultaneously. That is, there are disadvantages that an absorbent resin having a high gel strength possesses a low absorption capacity, the absorbent resin having a high absorption capacity possesses a low absorption rate because of gel blocking phenomenon or low gel strength after absorption. Attempts have been made to increase the absorption rate by decreasing the particle size of the absorbent resin, granulating the absorbent resin, or forming the absorbent resin in flakes. Generally, when the absorbent resin is formed in a small particle size, the resin particles on contact with urine convert themselves into what resembles wetted clusters of flour possibly to an extent of lowering the absorption rate. When the absorbent resin is formed in the form of granules, there ensues a phenomenon that the granules themselves independently convert into wetted clusters on contact with urine and the absorption rate is lowered. When the absorbent resin is formed in the form of flakes, though the absorption rate is fairly improved because the gel blocking does not occur, the absorption rate is not sufficient and the production of the absorbent has a restriction from the standpoint of process because the formation of the absorbent resin in the form of flakes is not economical because the produced absorbent resin inevitably becomes bulky and necessitates larger facilities for transportation and storage.

On the other hand, a technique for improving the absorption rate and the gel strength after absorption is by crosslinking molecule chain on the surface region of the absorbent resin to increase the crosslinking degree of the surface region without substantially decreasing the absorption capacity.

These techniques have been disclosed in Japanese Patent Laid-Open SHO 57(1982)-44,627, Japanese Patent Laid-Open SHO 58(1983)-42,602, Japanese Patent Publication SHO 60(1985)-18,690, Japanese Patent Laid-Open SHO 58(1983)-180,233, Japanese Patent Laid-Open SHO 59(1984)-62,665 and Japanese Patent Laid-Open SHO 61(1986)-16,903, for example. The absorption rate and gel strength after absorption can be improved by the above mentioned surface treating techniques, but there are some disadvantages in that it requires a large amount of an organic solvent or is insufficient in mixing when the surface treating agent is mixed with the absorbent resin.

On the other hand, recently, it has been found that the water retaining property and absorption rate under pressure are required as properties of the absorbent resin. Further, when the absorbent resin is used for a disposable diaper, the absorbent resin is used by dispersing among the pulp fibers, and liquid high permeability is required in such a case.

Accordingly, an object of the present invention is to provide a novel method of treating the surface of an absorbent resin which is industrially and economically excellent.

An object of the present invention is to provide a method of treating the surface of the absorbent resin which is effective for obtaining an absorbent possessing high absorption rate under pressure and high water retaining property under pressure.

Still another object of the present invention is to provide a method of treating the surface of the absorbent resin which is effective for obtaining the absorbent possesing excellent liquid permeability when it is used by dispersing among pulp fibers and the like.

SUMMARY OF THE INVENTION

The objects described above are accomplished by a method of treating the surface of an absorbent resin powder, which comprises mixing (A) 100 parts by weight of an absorbent resin powder possessing a carboxyl group, (B) 0.01 to 20 parts by weight of a crosslinking agent (C) 0 to 50 parts by weight of water, and (D) 0 to 60 parts by weight of a hydrophilic organic solvent in a high-speed stirring type mixer provided with an inner surface formed substantially of a substrate possessing a contact angle of not less than about 60° with respect to water and a heat distortion point of not lower than about 70° and completing the reaction of the absorbent resin powder (A) with the cross-linking agent(B).

In accordance with the present invention, the absorbent resin powder (A) is ideally mixed with the cross-linking agent(B) and, as a result, the produced absorbent has high absorption rate under pressure and water retaining property under pressure and shows excellent liquid permeability when it is used by dispersing among the pulp fibers and the like.

EXPLANATION OF THE PREFERRED EMBODIMENT

Figure 1:
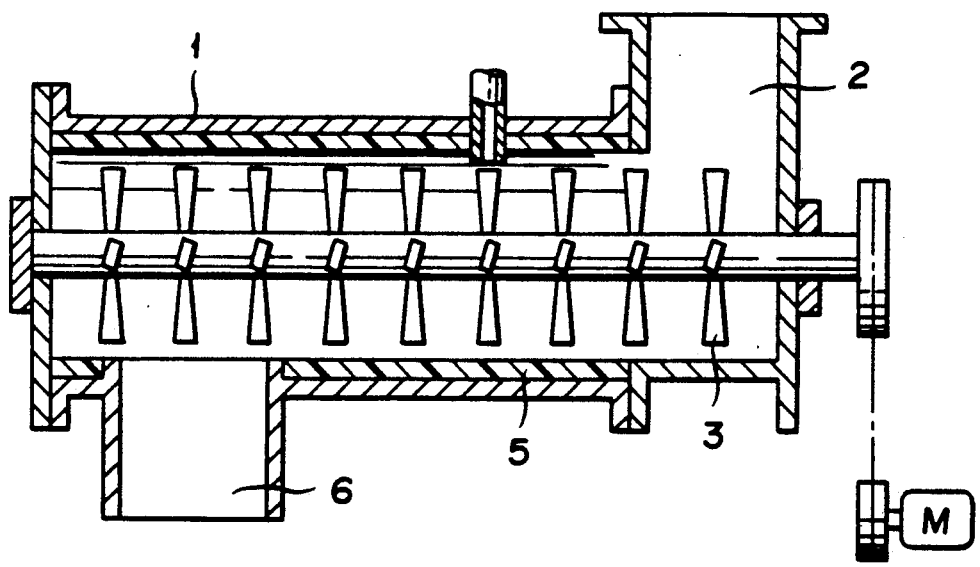
FIG. 1 is a sectional view of an embodiment of a mixer used in the present invention.

The absorbent resin powder (A) to be used in the present invention is required to possess a carboxyl group. The absorbent resin powders which answer this description include hydrolyzed starch-acrylonitrile graft copolymer, partially neutralized starch-acrylonitrile graft copolymer, saponified vinyl acetate-acrylic ester copolymers, hydrolyzed acrylonitrile copolymers or acrylamide copolymers, cross-linked products of the copolymers, partially neutralized polyacrylic acid, and cross-linked products of partially neutralized polyacrylic acid which are invariably in a powdered form, for example. These absorbent resin powders may be used either inependently or in the form of a mixture of two or more members. Though the absorbent resin powder (A) preferably possesses a cross-linked structure, it may be used effectively in a form destitute of such a cross-linked structure.

In the various powdered absorbent resins (A) mentioned above, those which prove to be particularly desirable are the absorbent resins to be shown below in (1) to (5).

(1) The powdery alkali metal acrylate polymer obtained by thermally drying a gel-like water-containing polymer formed by copolymerizing 100 parts by weight of an acrylic acid salt monomer comprising 1 to 50 mol % of acrylic acid and 99 to 50 mol % of an alkali metal acrylate and 0 to 5 parts by weight of a cross-linking monomer in an aqueous solution having a monomer concentration of not less than 20% by weight.

(2) The powdery resin obtained by dispersing the aqueous solution of acrylic acid and/or an alkali metal acrylate containing a water-soluble radical polymerization initiator and optionally a cross-linking monomer in an alicyclic and/or aliphatic hydrocarbon solvent in the presence of a surfactant possessing HLB in the range of 8 to 12 and suspension polymerizing the resultant dispersion.

(3) The powdery saponified copolymer of a vinyl ester with an ethylenically unsaturated carboxylic acid or a derivative thereof.

(4) The powdery absorbent resin obtained by polymerizing starch and/or cellulose, a monomer possessing a carboxyl group, or capable of forming a carboxylic group in consequence of hydrolysis and optionally a cross-linking monomer in an aqueous medium and optionally further hydrolyzing the resultant polymer.

(5) The powdery absorbent resin obtained by causing an alkali substance to react upon maleic anhydride copolymer comprising maleic anhydride and at least one monomer selected from the group consisting of α-olefins and vinyl compounds and optionally causing a polyepoxy compound to react with the resultant reaction product.

Though the amount of the carboxyl group possessed by the absorbent resin powder (A) is not specifically limited, the carboxyl group is preferably to be present in an amount of not less than 0.01 equivalent, based on 100 g of the absorbent resin powder (A). In the case of a partially neutralized polyacrylic acid, for example, the proportion of the unneutralized polyacrylic acid is preferably to be in the range of 1 to 50 mol %, preferably 5 to 40 mol %.

The shape of particles of the absorbent resin powder (A) to be used in the present invention is not specifically limited. It may be the sphere shape obtained by the reversed-phase suspension polymerization, the flake shape obtained by drum drying, or the indefinite shape particles obtained by pulverizing resin clusters.

The cross-linking agents (B) which are usable in the present invention include compounds possessing in the molecular unit thereof at least two functional groups capable of reacting with the carboxyl group and polyvalent metal compounds. The cross-linking agents which are usable as the component (B) in the present invention include polyhydric alcohols such as ethylene glycol, diethylene glycol, triethylene glycol, tetraethylene glycol, polyethylene glycol, glycerin, propylene glycol, diethanol amine, triethanol amine, polyoxy propylene, oxyethylene-oxypropylene block copolymer, pentaerythritol, and sorbitol, polyglycidyl ether compounds such as ethylene glycol diglycidyl ether, polyethylene glycol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether, and polypropylene glycol diglycidyl ether, polyaziridine compounds such as 2,2-bishydroxymethyl butanol-tris[3-(1-aziridinyl)proprionate], 1,6-hexamethylene diethylene urea, and diphenyl methane-bis-4,4'-N,N'-diethylene urea, haloepoxy compounds such as epichlorohydrin and α-methylfluorohydrin, polyamine compounds such as ethylene diamine, diethylene triamine, triethylene tetramine, tetraethylene pentamine, pantaethylene hexamine, and polyethylene imine, polyisocyanate compounds such as 2,4-toluylene diisocyanate and hexamethylene diisocyanate, hydroxides of zinc, calcium, magnesium, aluminum, iron, and zirconium, halogenides, and polyvalent metal compounds such as salts (represented by sulfates), for example. One cross-linking agent or two or more mutually unreactive cross-linking agents selected from the group mentioned above may be used.

Among other compounds mentioned above, those compounds possessing in the molecular unit thereof at least two functional groups capable of reacting with a carboxylic group prove to be particularly desirable. It is particularly preferable to use at least one compound selected from the group consisting of diethylene glycol, triethylene glycol, polyethylene glycol, glycerin, polyglycerin, propylene glycol, diethanol amine, triethanol amine, polyoxy propylene, oxyethylene-oxypropylene block copolymer, sorbitan fatty acid esters, polyoxyethlene sorbitan fatty acid esters, trimethylol propane, pentaerythritol, and sorbitol.

The proportion of the cross-linking agent (B) to be used in this invention is in the range of 0.01 to 30 parts by weight, preferably 0.1 to 10 parts by weight. So long as this proportion is in this range, the produced absorbent excels in absorption rate under pressure, water retaining property under pressure, and liquid permeability. If the proportion exceeds 30 parts by weight, the excess is wasted without producing any economic effect and suffered to overburden the accomplishment of a proper cross-linking effect and decrease the absorption capacity of the produced absorbent. Conversely, if this proportion is less than 0.01 part by weight, the effect of this invention is attained only with difficulty.

In the present invention, water (C) may be used during the mixing of the absorbent resin powder (A) with the cross-linking agent (B). The water (C) functions to promote uniform dispersion of the cross-linking agent (B) on the surface of the absorbent resin powder (A) and permeation of the cross-linking agent (B) in the surface region of the particles of the absorbent resin powder (A). When the polyvalent metal compound is used as the cross-linking agent (B), the water (C) is effective in promoting the reaction of the cross-linking agent (B) with the absorbent resin powder (A). It is preferable in this case to use the water (C).

In the present invention, when water (C) is used during mixing of the absorbent resin powder (A) and the cross-linking agent (B), an absorbent having higher absorption rate under pressure, higher water retaining property under pressure, compared to one without using water (C) can be obtained. That is, in the present invention, an amount of water to be used is in the range of 0 to 50 parts by weight, preferably 0.5 to 40 parts by weight, more preferably 2 to 40 parts by weight of the absorbent resin. If the amount of water (C) exceeds 50 parts by weight, the heat treatment consumes an unduly long time and the cross-linking agent (B) is caused to permeate to the cores of the particles of the absorbent resin powder (A) and the absorption capacity of the produced absorbent will decrease too much. Further, the absorbent resin powder (A) tends to form wetted clusters and the mixing will not be uniform.

The hydrophilic organic solvent (D) which is optionally used in the present invention is only required to be such that it will uniformly mix with the cross-linking agent (B) and refrain from producing any adverse effect upon the quality of the absorbent resin powder (A). The hydrophilic organic solvents which answer this description include lower alcohols such as methanol, ethanol, n-propanol, isopropanol, n-butanol, isobutanol, sec-butanol, and t-butanol, ketones such as acetone, methylethyl ketone, and methylisobutyl ketone, ethers such as dioxane, tetrahydrofuran, and diethyl ether, amides such as N,N-dimethyl formamide and N,N-diethyl formamide, and sulfoxides such as dimethyl sulfoxide, for example. The hydrophilic organic solvent (D) functions to effect uniform dispersion of the cross-linking agent (B) and the optionally used water (C) on the surface of the absorbent resin powder (A).

The amount of the hydrophilic organic solvent (D) to be used in the present invention is in the range of 0 to 60 parts by weight, preferably 0.1 to 10 parts by weight, based on 100 parts by weight of the absorbent resin powder (A), though the amount is variable with the kind and particle size of the absorbent resin powder (A) to be used. If the amount of the hydrophilic organic solvent (D) exceeds 60 parts by weight, the excess is not observed to give a proportionate addition to the effect aimed at but is suffered to impair the economy by increasing the amount of energy to be spent for the purpose of drying. For this invention, the use of the hydrophilic organic solvent (D) is not always necessary because the mixture of the absorbent resin powder (A) with the cross-linking agent (B) is carried out by the use of a specific high-speed stirring type mixer which will be described more fully hereinafter. There are times when the use of the hydrophilic organic solvent (D) will result in an enhanced effect of this invention, depending on the kind and the amount of the cross-linking agent (B) or on the amount of water (C) or the kind and the particle size of the absorbent resin powder (A) to be used. If the mixing of the absorbent resin powder (A) with the cross-linking agent (B) is insufficient, for example, if the particle size of the absorbent resin powder (A) and if the amount of water (C) to be used is larger compared to the amount of the cross-linking agent (B) to be used, the effect of the present invention is apt to be obtained by using a comparatively small amount of the hydrophilic organic solvent (D).

In this invention, the mixing of the absorbent resin powder (A) with the cross-linking agent (B) is carried out by the use of a high-speed stirring type mixer which is provided with an inner surface formed substantially of a substrate (I) possessing a contact angle of not less than about 60° with respect to water and a heat distortion point of not lower than about 70° C., preferably not lower than about 100° C.

The high-speed stirring type mixer to be used in the present invention has at least one stirring shaft possessing at least one stirring blade, and can be rotated at not less than about 600 m/minute of the lead-end peripheral speed of the stirring blade.

The high-speed stirring type mixers include mixers of the type provided on the bottom inside a stirring tank thereof with rotary blades such as, for example, Henschel Mixer [produced by Mitsui Miike Machinery Co., Ltd.], New Speed Mixer [produced by Okada Seiko K.K.] and Heavy-Duty Matrix [produced by Nara Kikai Seisakusho K.K.] and mixers of the type capable of (continuously) mixing two or more kinds of powder or a powder with a liquid by the high-speed rotation of a rotar provided with a multiplicity of paddles and disposed inside a cylindrical container such as, for example, Turbulizer and Sand Turbo (both produced by Hosokawa Micron K.K.). Among these high-speed stirring type-mixers, a continuous type mixer is preferable because of its high productivity.

The Turbulizer, for example, has a lining of substrate (I) formed on the inner surface of or a sleeve 5 of the substrate (I) inserted in a horizontal cylindrical main body 4 which is provided with an absorbent resin powder inlet 1, an absorbent resin powder outlet 2, and a treating liquid inlet 3 as illustrated in FIG. 1. The main body 4 is provided therein with a high-speed rotary paddle 6. Optionally, a lining of substrate (I) is formed on the inner surface of or a sleeve 8 of the substrate (I) is inserted in the absorbent resin powder outlet 2.

As already pointed out, it is essential that the high-speed stirring type mixer to be used in this invention should be provided with an inner surface formed substantially of a substrate (I) possessing a contact angle of not less than about 60° with respect to water and a heat distortion point of not lower than about 70° C.

If the contact angle of the substrate (I) relative to water is less than about 60°, the mixing of the absorbent resin powder (A) with the cross-linking agent (B) does not take place ideally. If the heat distortion point is lower than about 70° C., the substrate (I) is incapable of withstanding the heat to be generated during the course of mixing, with the result that no stable mixing can be continued.

The substances which are usable as the substrate (I) for the formation of the inner surface of the mixer include synthetic resins such as polyethylene, polypropylene, polyester, polyamide, fluorine resin, polyvinyl chloride, epoxy resin, and silicone resin and the synthetic resins mentioned above which are complexed and reinforced with inorganic fillers such as glass, graphite, bronze, and molybdenum disulfide and organic fillers such as polyimide, for example. Among other substances mentioned above, fluorine resins such as polyethylene tetrafluoride, polyethylene trifluoride, polyethylene trifluorochloride, ethylene tetrafluoride-ethylene copolymer, ethylene trifluorochloride-ethylene copolymer, propylene pentafluoride-ethylene tetrafluoride copolymer, perfluoroalkylvinyl ether-ethylene tetrafluoride copolymer, polyvinylidene fluoride, and polyvinyl fluoride, for example, are particularly preferable.

The high-speed stirring type mixer to be used in this invention may have the mixer itself formed of the substrate (I) mentioned above. Generally, the mixer is formed of a metal material and has the inner wall thereof lined with a coating of the substrate (I) or covered with a sleeve of the substrate (I).

Preferably, a shaped material, more preferably a shaped cylindrical material comprising the substrate (I) is inserted into the high-speed stirring type mixture.

Further, the shaped material of the substrate (I) has preferably not less than 5 mm, more preferably not less than 10 mm of thickness. When the absorbent resin powder (A) is mixed with the cross-linking agent (B) for a long time, if the mixer wherein the inner surface of the mixer is coated with the substrate (I) is used, the layer of the substrate (I) is defaced because of insufficient thickness within a comparatively short time and the foundation appears, so the mixing becomes unstable. In addition, the coating layer requires more time and cost when it is repaired. On the contrary, when the shaped material of the substrate (I) having not less than 5 mm of the thickness is detachably inserted into the mixer, the mixture can be stably obtained even for a long time, and the repairing can be easily carried out.

Japanese Patent Laid-Open SHO 61(1986)-16,903 discloses a method which comprises mixing an absorbent resin powder, a cross-linking agent, and water or an aqueous compound prepared by substituting a hydrophilic organic solvent for water by the use of a rotary paddle type mixer and subjecting the resultant mixture to a heat treatment thereby inducing cross-linking of molecular chains near the surface regions of the particles of the absorbent resin powder. It has been found, however, that the rotary paddle type mixer not provided with the inner surface formed of the substrate (I) mentioned above is incapable of attaining ideal mixture of the absorbent resin powder (A), the cross-linking agent (B), water (C), and the hydrophilic organic solvent (D). When the absorbent resin powder (A) and the cross-linking agent (B) are mixed by the use of the rotary paddle type mixer under the conditions for manifestation of the effect of this invention, namely when the mixing is carried out in the presence of 0.5 to 40 parts by weight of water (C) based on 100 parts by weight of the absorbent resin powder (A), the materials being mixed adheres strongly to the inner wall of the cylindrical vessel, the state of this adhesion changing from time to time, rendering it impossible to control the condition of mixture at a fixed level at all times.

If this adhesion gains in strength, the mixer is overburdened in a large measure and, in an extreme case, brought to a stop. Further, since the mixing does not proceed in an ideal state, the produced absorbent is deficient in absorption rate under pressure, water retaining property under pressure, and liquid permeability.

Although the exact reason why the absorbent obtained by the present invention can enjoy the extremely higher performance than the standard which can be expected based on the above mentioned known technology, it is thought that the reaction of the absorbent resin powder (A) with the crosslinking agent (B) is different in the reaction under microscopically heterogeneous state in addition to microscopical homogenuity of the mixing of the absorbent resin powder (A) with the crosslinking agent (B).

In the present invention, when the absorbent resin powder (A) and the crosslinking agent (B) are mixed by the use of the high-speed stirring type mixer, they may be used in conjunction with a water-insoluble fine powder (hereinafter referred to as "powder (E)"). The additional use of the powder (E) serves the purpose of amply heightening the effect of mixing.

The water-insoluble fine powders (E) which are usable herein include organic powders such as carbon black and activated carbon which are effective in improving the lightfastness of the absorbent resin and also capable of producing an odorizing effect, pulp powder, and fine crosslinked acryl polymer and inorganic powders such as talc, pyrophylite, kaolinite, hulsite, and other similar clay minerals, and Aerosil 200 (produced by Nippon Aerosil K.K) comprising mainly of silicon dioxide particles having an average particle size of not more than 50 $\mu$m, and carplex #80 (produced by Shionogi & Co., Ltd.), for example. The particle size of these water insoluble fine powders (E) is in the range of not more than 1000 $\mu$m, preferably not more than 100 $\mu$m, more preferably not more than 50 $\mu$m.

The amount of the water-insoluble fine powder (E) to be used is in the range of 0.01 to 10 parts by weight, preferably 0.01 to 5 parts by weight, based on 100 parts by weight of the absorbent resin powder (A). So long as the amount is in the range mentioned above, the absorbent which excels in absorption rate under pressure, water retaining property under pressure, and liquid pemeability can be obtained efficiently. If this amount exceeds 10 parts by weight, the excess does not produce any proportionate addition to the effect but rather impairs the absorption capacity. Especially, according to the present invention, the absorbent resin having higher water retaining property under pressure can be preferably obtained by using water (C), but if the amount of water (C) to be used is too large, mixing of the absorbent resin powder (A) with the crosslinking agent (B) becomes insufficient. In such a case, addition of a small amount of the water insoluble fine powder (E) sometimes improves the mixing property. Especially, when both water insoluble powder (E) and hydrophilic organic solvent (D) are used, the improvement in the mixing becomes higher.

When the absorbent resin powder (A) and the crosslinking agent (B) are mixed in conjunction with the water-insoluble fine power (E), this powder (E) may be directly fed to the high-speed stirring type mixer similarly to the absorbent resin powder (A) and the crosslinking agent (B) so as to participate in the mixing from the beginning. Optionally, the powder (E) may be premixed with the absorbent resin powder (A) in a varying mixer and then the resultant premix and the crosslinking agent (B) may be fed to the high-speed stirring type mixer to be mixed therein. Alternatively, the powder (E) may be mixed with the cross-linking agent (B) to obtain a mixture, and then the mixture may be mixed with the absorbent resin powder (A). When the powder (E) is used, as well as when it is not used, the mixing may be carried out in the presence of water (C) and/or the hydrophilic organic solvent (D). Particularly, water (C) at times serves the purpose of enhancing the effect derived from the use of the powder (E).

The method of treating the surface of the present invention can be attained by mixing the components (A) to (E) and reacting the surface region of the absorbent resin powder (A) with the crosslinking agent (B). In such case, the reaction with the crosslinking agent (B) may be carried out during and/or after mixing. When the reaction necessitates application of heat as when a polyhydric alcohol, a polyglycidyl compound, a polyamine compound, or a polyoxazoline compound is used as the crosslinking agent (B), the heat treatment is desired to be carried out after the absorbent resin powder (A) and the crosslinking agent (B) have been mixed. The temperature of the heat treatment is generally in the range of 40° to 250° C., preferably in the range of 90° to 250° C. When a polyaziridine compound, a polyisooyanate compound, or a polyvalent metal compound is used as the crosslinking agent (B), though the heat treatment is not particularly necessary, it may be performed for the purpose of further ensuring the reaction.

The heat treatment can be carried out by the use of an ordinary drier or heating furnace. The driers which are usable for the heat treatment include a horizontal stirring drier, rotary drier, disc drier, a kneading drier, a fluidized-bed drier, an air-current drier, and an infrared drier, for example. The heat treatment may be started immediately after the completion of the mixing or after the product of the mixture has been left standing for a prescribed time.

Although the mixing of the absorbent resin powder (A) with the crosslinking agent (B) may be carried out under the condition of either stirring or non-stirring, the mixing under the condition of the stirring is preferable because the reaction can proceed homogeneously.

The temperature of the heat treatment is as already described. When a polyhydric alcohol is used as the crosslinking agent (B) and the heating temperature is selected in the range of 90° to 250° C., preferably about 170° to about 220° C., the crosslinking reaction enough for sufficient manifestation of the effect of this invention can be effected quickly without entailing the possibility of the absorbent resin being colored or deteriorated. It should be noted parenthetically that when the heat treatment is carried out at a high temperature exceeding 250° C., the absorbent resin may succumb to thermal deterioration, depending on the kind of the resin.

When the absorbent resin powder (A) is reacted with the crosslinking agent (B), the effect of the present invention can be exhibited more remarkably by reacting until the time when the reaction is completed. The time when the reaction is completed is the time which satisfies the equations (a-1), (a-2), (b-1) or (b-2) (Where the water-insoluble fine powder (E) is not used during the course of mixing)

$$30 \leq \frac{(100 + R)}{100} \times \frac{Q}{P} \times 100 \leq 95 \qquad (a\text{-}1)$$

preferably $$40 \leq \frac{(100 + R)}{100} \times \frac{Q}{P} \times 100 \leq 80 \qquad (a\text{-}2)$$

wherein P is absorption capacity of absorbent resin powder (A) using physiological saline solution, Q is absorption capacity of resultant treated absorbent resin using physiological saline solution, and R is the amount, in parts by weight, of cross-linking agent (B) to be used based on 100 parts by weight of absorbent resin powder (A). (Where the water-insoluble fine powder (E) is used during the course of mixing)

$$30 \leq \frac{(100 + R + S)}{100} \times \frac{Q}{P} \times 100 \leq 95 \qquad (b\text{-}1)$$

preferably $$40 \leq \frac{(100 + R + S)}{100} \times \frac{Q}{P} \times 100 \leq 80 \qquad (b\text{-}2)$$

wherein P is absorption capacity of absorbent resin powder (A) using physiological saline solution, Q is absorption capacity of resultant treated absorbent resin using physiological saline solution, R is the amount, in parts by weight, of cross-linking agent (B) based on 100 parts by weight of absorbent resin powder (A), and S is the amount, in parts by weight, of water-insoluble fine powder (E) based on 100 parts by weight of absorbent resin powder (A).

If the reaction is continued until the calculation value of the above mentioned equations (a-1) or (b-1) becomes not more than 95, the absorbent thus obtained is increased in absorption rate under pressure and water retaining property under pressure, it is more preferable that the reaction is proceeded until the value becomes not more than 80. Especially, when a polyhydric alcohol is used as the cross-linking agent (B), absorption rate under pressure and water retaining property under pressure was insufficient by the conventional techniques, but the absorbent obtained by the present invention has excellent absorption rate under pressure and water retaining property under pressure.

On the contrary, if the calculation value of the above mentioned equation (a-1) or (b-2) is less than 30, the cross-linking becomes excess in attainment of the appropriate cross-linking effect, and the absorbent thus obtained becomes lower in the absorption capacity.

The absorbent obtained by the present invention shows high absorption rate under pressure and high liquid permeability and is excellent in water retaining property under pressure.

Therefore, the absorbent is useful not only as one of the component materials of such sanitary articles as sanitary napkins and disposable diapers but also as a coagulant for sludge, as a dew-drop proofing agent for building materials, as a water-proofing agent for agriculture and horticulture, and as a dryer.

Now, the present invention will be described more specifically with reference to working examples. It should be noted, however, that the scope of this invention is not limited to these examples.

EXAMPLE 1

A jacketed twin arm type kneader of stainless steel measuring 10 liters in inner volume, 220 mm×240 mm in the opening, and 240 mm in depth, and provided with two Sigma type blades possessing a rotational diameter of 120 mm was stoppered with a lid. Into this kneader, a monomer component containing 5,500 g of an aqueous solution of sodium acrylate possessing a neutralization ratio of 75 mol % and 1.36 g of trimethylol propane triacrylate 0.020 mol % based on sodium acrylate possessing a neutralization ratio of 75 mol %) (the monomer concentration 37% by weight in the aqueous solution) was introduced and nitrogen gas was blown to displace the air entrapped inside the reaction system.

Then, the two Sigma type blades were set rotating at rates of 46 rpm and, at the same time, the jacket was heated by passage of hot water at 35° C. As a polymerization initiator, 2.8 g of sodium persulfate and 0.14 g of L-ascorbic acid were added. Polymerization started four minutes after the addition of the polymerization initiator. The peak temperature inside the reaction system reached 82° C. after the elapse of 15 minutes following the addition of the polymerization initiator. The hydrated gel polymer had been divided into minute particles about 5 mm in size. The stirring was further continued. The lid was removed from the kneader 60 minutes after the start of the polymerization and the gel was removed from the kneader.

The minute particles of hydrated gel polymer thus obtained were spread on a 50-mesh metal gauze and dried with hot air at 150° C. for 90 minutes. The dried minute particles were pulverized with a hammer type crusher and sifted with a 20-mesh metal gauze to obtain a 20-mesh pass portion [absorbent resin powder (A-1)].

In a Turbulizer 1 (produced by Hosokawa Micron K. K.) fitted with an inner tube 5 made of polytetrafluoroethylene (contact angle 114° C. and heat distortion point 121° C.) having 10 mm in thickness as shown in FIG. 1, grams of the absorbent resin powder (A-1) was changed continuously from a powder inlet 2 and a liquid mixture of glycerol and water was continuously charged from a liquid inlet 4 at a rate of 1 part of glycerol, 3 parts of water, and 1 part of isopropanol per 100 parts of the absorbent resin powder (A-1) and the mixture was mixed. The rotation number of the stirring blade of the Turbulizer was 3,000 rpm.

The resultant mixture discharged from an outlet 6 was charged into a bowl dipped in an oil bath (195° C.) and was subjected to heat-treatment for 40 minutes under stirring to obtain an absorbent (1).

The absorbent resin powder (A-1) and the absorbent (1) obtained as described above were tested for (i) absorption capacity, (ii) water-retaining property under pressure 10 min and 30 min, and (iii) liquid permeability as follows;

(i) Absorption capacity: A pouch (40 mm×150 mm) made of non-woven fabric after the fashion of a tea bag and filled evenly with about 0.2 g of a sample of absorbent resin powder (A-1) or absorbent (1) was immersed in an aqueous 0.9% NaCl solution for 60 min removed from the solution, left draining for 5 sec, further removing water on 24folded toilet paper having 60 cm for 10 seconds and weighed.

$$\text{Absorption Capacity(g/g)} = \frac{\text{Weight after absorption(g)} - \text{Blank(g)}}{\text{Weight of absorbent resin(g)}}$$

Figure 2:
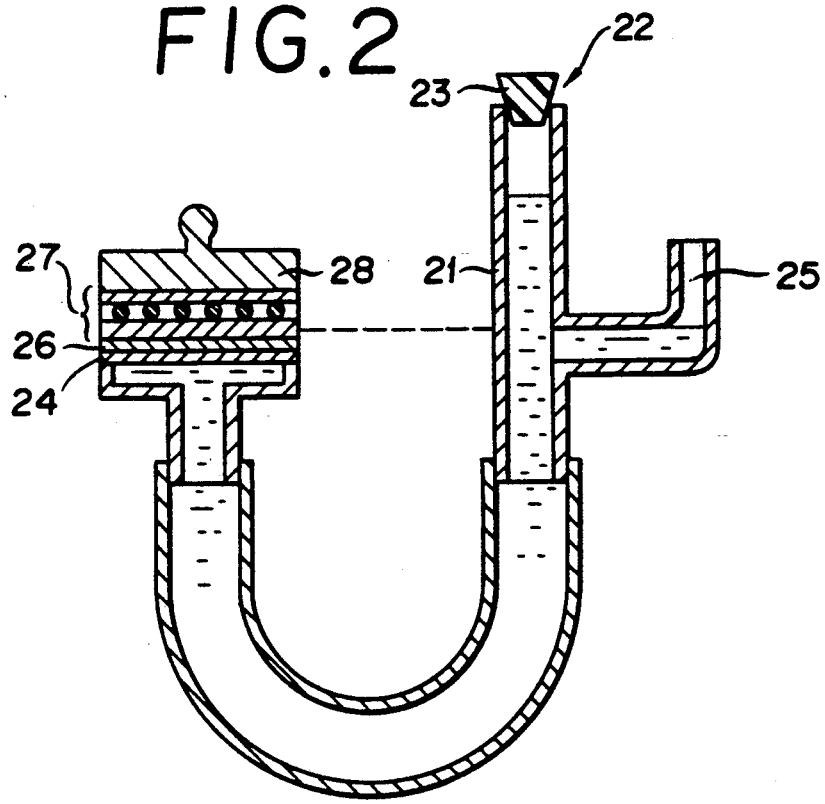
FIG. 2 is a sectional view of an apparatus for measuring water-retaining property under pressure.

(ii) Water-retaining property under pressure: The test for the water-retaining property under pressure was carried out by the use of an apparatus configured as shown in FIG. 2. The upper end 22 of a buret 21 was stoppered with a plug 23 and a measuring stand 24 was set flush with an air inlet 25. On a glass filter (No. 1) 26 70 mm in diameter placed in the measureing stand 24, a filter paper, 0.20 g of a sample of absorbent resin powder (A-1) or absorbent (1), and a filter paper 27 were superposed and a weight of 0.2 psi was mounted thereon. The sample as sandwiched between the filter papers was left to absorbing synthetic urine (containing 1.9% of urea, 0.8% of NaCl, 0.1% of $CaCl_2$, and 0.1% of $MgSO_4$) for 10 or 30 minutes. At the end of the absorption, the volume (A ml) of the synthetic urine absorbed was measured.

Water-retaining property = $A$(ml)/0.20(g)

under pressure (ml/g)

Figure 3:
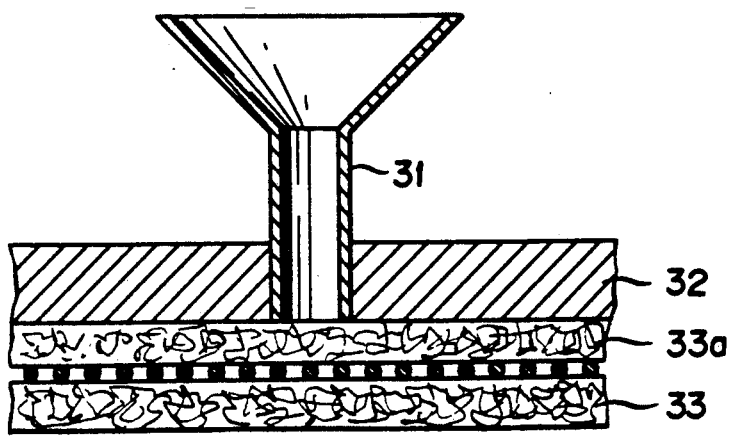
FIG. 3 is a sectional view of an apparatus for measuring liquid permeability.

(iii) Liquid permeability: The test for liquid permeability was carried out by the use of an apparatus configured as shown in FIG. 3. A model diaper was prepared by uniformly scattering 4.0 g of a sample of absorbent resin powder (A-1) or absorbent (1) 34 on a bed of 12 g of pulp 33 140 mm×250 mm, in area, superposing 12 g of pulp 33a on the scattered sample, and pressing the superposed layers under a load of 2 $kg/cm^2$. A weight 32 of 0.2 psi measuring 140 mm×250 mm in area and provided at the center thereof with a synthetic urine 31 was mounted on the model diaper. Then 100 ml of the synthetic urine was poured into the model diaper. After standing for 30 minutes, further when 150 ml of a synthetic urine is introduced, the time which elapsed before the synthetic urine disappeared from the inlet was clocked.

(v) Calculated value of formula: Water content (105° C., 3 hrs) of the absorbent powder (A-1) was 2% (wet basis), the value $P/0.98 = P'$ was inserted into the equation (a-1) to calculate the value of the equation. Further, water content of absorbent (1) was 0%.

EXAMPLE 2

A similar method to Example 1 was repeated to obtain an absorbent (2) except that a Turbulizer using a high density poyethylene tube instead of the inner tube 5 was used. A similar test to Example 1 was carried out and the results are shown in Table 1.

CONTROL 1

A similar method to Example 1 was repeated to obtain a control absorbent (1) except that the Turbulizer without the inner tube 5 was used. A similar test to Example 1 was carried out and the results are shown in Table 1.

CONTROL 2

A similar method to Example 1 was repeated to obtain a control absorbent (2) except that a mortar mixer provided with a tetrafluoroethylene-perfluoroalkyl vinyl ether copolymer coated inner wall was used instead of the Turbulizer used in Example 1. The stirring blade of the mortar mixer rotated at the maximum rotation number, but the leading-end peripheral speed of the stirring blade was 185 m/minutes. A similar test to Example 1 was carried out and the results are shown in Table 1.

EXAMPLE 3

A pulverized hydrated gel was obtained by the procedure of Example 1, except that 1.7 g of trimethylol propane triacrylate (0.025 mol % based on sodium acrylate possessing a neutralization ratio of 75 mol %) was used. The gel was dried and crushed by a similar method as in Example 1 to obtain a powder that passed through a 20-mesh metal gauze[absorbent resin powder (A-2)].

In a Turbulizer 1 fitted with an inner tube 5 made of polytetraflurorethylene (contact angle 114° and heat distortion point 121° C.) having 10 mm in thickness as shown in FIG. 1, 100 parts of the aborbent resin powder (A-2) was charged continuously from a powder inlet 2 and a liquid mixture of 0.1 part of ethylene glycol diglycidyl ether, 8 parts of water and 1 part of isopropanol was charged from a liquid inlet 4 and the mixture was mixed.

The resultant mixture discharged from an outlet 6 was charged into a bowl dipped in an oil bath 120° C.) and was subjected to heat-treatment for 60 minutes under stirring to obtain an absorbent (3).

The absorbent resin powder (A-2) and the absorbent (3) obtained as described above are tested by a method similar to Example 1 and the results are shown in Table 1.

EXAMPLE 4

100 Parts by weight of the absorbent resin powder (A-2) was mixed with 0.5 parts by weight of the water-insoluble fine silica ("Aerosil 200", a trade name of a product of Aerosil Co., Ltd.) in a V-type mixer to obtain an absorbent resin power B.

A similar method to Example 3 was carried out to obtain an absorbent (4) except that the absorbent resin power B was used instead of the absorbent resin power (A-2). A similar test to Example 1 was carried out and the results are shown in Table 1.

TABLE 1

|  | Absorbent Resin Powder A-1 | Example 1 | Example 2 | Control 1 | Control 2 | Absorbent Resin Powder A-2 | Example 3 | Example 4 |
|---|---|---|---|---|---|---|---|---|
| Precursor |  | A-1 | A-1 | A-1 | A-1 |  | A-2 | A-2 |
| Absorption Capacity | 62 | 62 | 62 | 62 | 62 | 54 | 54 | 54 |
| Precursor (parts) |  | 100 | 100 | 100 | 100 |  | 100 | 100 |
| Cross linking Agent |  | glycerol | glycerol | glycerol | glycerol |  | EGDGE | EGDGE |
| Cross linking Agent (parts) |  | 1 | 1 | 1 | 1 |  | 0.1 | 0.1 |
| Water (parts) |  | 3 | 3 | 3 | 3 |  | 8 | 8 |
| Hydrophilic Organic Solvent (parts) |  | 1 | 1 | 1 | 1 |  | 1 | 1 |
| Mixer |  | Turb | Turb | Turb | Mortar 120 rpm |  | Turb | Turb |
| Inner Substrate |  | PTFE | HDPE | SUS 304 | PFA |  | PTFE | PTFE |
| Contact Angle (dgree) |  | 114 | 88 | 10 | 115 |  | 114 | 114 |
| Heat Distortion (°C.) |  | 121 | 82 | >200 | 75 |  | 121 | 121 |
| Peripheral speed (m/min.) |  | 1280 | 1280 | 1280 | 185 |  | 1280 | 1280 |
| Absorbent Propeties |  |  |  |  |  |  |  |  |
| Absorption Capacity (g/g) |  | 44 | 45 | 46 | 46 |  | 47 | 48 |
| Water-retaining property under pressure (ml/g) |  |  |  |  |  |  |  |  |
| 10 min. | 7.5 | 24 | 23 | 18 | 16 | 8 | 22 | 23 |
| 30 min. | 9.5 | 29 | 28 | 22 | 21 | 10 | 26 | 27 |
| Liquid Permeability (sec) | 190 | 80 | 85 | 95 | 110 | 170 | 90 | 85 |
| Calculated Value of Formula |  | 70 | 70 | 73 | 73 |  | 85 | 86 |

What is claimed is:

1. A method of treating the surface of an absorbent resin, which comprises mixing (A) 100 parts by weight of an absorbent resin powder possessing a carboxyl group, (B) 0.01 to 30 parts by weight of a cross-linking agent, said cross-linking agent possessing at least two functional groups capable of reacting with a carboxyl group, (C) 0 to 50 parts by weight of water, and (D) 0 to 60 parts by weight of a hydrophilic organic solvent in a high-speed stirring type mixer provided with an inner surface formed substantially of a substrate (I) possessing a contact angle of not less than about 60° with respect to water and a heat distortion point of not lower than about 70° C. under a condition of not less than about 600 m/minute of a lead-end peripheral speed of a stirring blade and completing reaction of said absorbent resin powder (A) with said cross-linking agent (B).

2. A method according to claim 1, wherein said inner surface is a shaped material of said substrate (I) detachably inserted into said mixer.

3. A method according to claim 2, wherein said inner surface of the high-speed stirring type mixer has a thickness of not less than 5 mm.

4. A method according to claim 2, wherein said shaped material is cylindrical.

5. A method according to claim 1, wherein said substrate (I) is one member selected from the group consisting of polyethylene, polypropylene, polyesters polyamides, fluorine resin, polyvinyl chloride, epoxy resin, and silicone resin.

6. A method according to claim 5, wherein said substrate (I) is a fluorine resin.

7. A method according to claim 1, wherein said cross-linking agent (B) is a compound which possesses at least two functional groups capable of reacting with a carboxyl group in the molecular unit thereof.

8. A method according to claim 7, wherein said cross-linking agent (B) is selected from the group consisting of polyhydric alcohol compounds, polyglycidyl ether compounds, polyoxazoline compounds, and polyamine compounds.

9. A method according to claim 1, wherein said cross-linking agent (B) is used in an amount in the range of 0.1 to 10 parts by weight, based on 100 parts by weight of said absorbent resin powder (A).

10. A method according to claim 1, wherein said water (C) is used in an amount in the range of 0.5 to 40 parts by weight, based on 100 parts by weight of said absorbent resin powder (A).

11. A method according to claim 1, wherein said hydrophilic organic solvent (D) is used in an amount in the range of 0.1 to 10 parts by weight, based on 100 parts by weight of said absorbent resin powder (A).

12. A method according to claim 1, wherein said water (C) is used in an amount in the range of 0.5 to 40 parts by weight and said hydrophilic organic solvent (D) is used in an amount in the range of 0.1 to 10 parts by weight per 100 parts by weight of said absorbent resin powder (A).

13. A method according to claim 7, wherein the time for completion of the reaction is the time that satisfies the following equation (a-1):

$$30 \leq \frac{(100 + R)}{100} \times \frac{Q}{P} \times 100 \leq 95 \quad \text{(a-1)}$$

wherein P is absorption capacity of absorbent resin powder (A) using physiological saline solution, Q is absorption capacity of the resultant treated absorbent resin using physiological saline solution, and R is the amount, in part by weight, of said cross-linking agent (B) based on 100 parts by weight of said absorbent resin powder (A).

14. A method according to claim 13, wherein the time for completion of the reaction is the time that satisfies the following equation (a-2):

$$40 \leq \frac{(100 + R)}{100} \times \frac{Q}{P} \times 100 \leq 80 \quad \text{(a-2)}$$

15. A method according to claim 7, wherein said the reaction temperature is in the range of 40° to 250° C.

16. A method according to claim 7, wherein said crosslinking agent (B) is polyhydric alcohol compounds.

17. A method according to claim 16, wherein 100 parts by weight of said absorbent resin powder (A), 0.1 to 10 parts by weight of said crosslinking agent (B), 0.5 to 40 parts by weight of water (C) and 0 to 60 parts by weight of said hydrophilic organic solvent (D) are mixed, and the reaction is carried out until the reaction is completed, wherein the time for completion of the reaction is the time that satisfies the following equation (a-1):

$$30 \leq \frac{(100 + R)}{100} \times \frac{Q}{P} \times 100 \leq 95 \quad \text{(a-1)}$$

wherein P is absorption capacity of absorbent resin powder (A) using physiological saline solution, Q is absorption capacity of the resultant treated absorbent resin using physiological saline solution, and R is the amount, in part by weight, of said cross-linking agent (B) based on 100 parts by weight of said absorbent resin powder (A).

18. A method according to claim 17, wherein the time for completion of the reaction is the time that satisfies the following equation (a-2):

$$40 \leq \frac{(100 + R)}{100} \times \frac{Q}{P} \times 100 \leq 80 \quad \text{(a-2)}$$

19. A method according to claim 16, wherein the reaction temperature is in the range of 90° to 250° C.

20. Substantially water-insoluble, absorbent, hydrogel-forming, polymer produced in accordance with the method of claim 1, 7, 13, 16 or 17.

21. A method according to claim 1, wherein mixing of said absorbent resin powder (A) with said cross-linking agent (B) is carried out in the presence of 0.01 to 10 parts by weight of a water-insoluble fine powder (E) based on 100 parts by weight of said absorbent resin powder (A).

22. A method according to claim 21, wherein the time for completion of the reaction is the time that satisfies the following equation (b-1):

$$30 \leq \frac{(100 + R + S)}{100} \times \frac{Q}{P} \times 100 \leq 95 \quad \text{(b-1)}$$

wherein P is absorption capacity of absorbent resin powder (A) using physiological saline solution, Q is absorption capacity of the resultant treated absorbent resin using physiological saline solution, and R is the amount, in part by weight, of said cross-linking agent (B), and S is the amount, parts by weight, of said water-insoluble fine powder (E), based on 100 parts by weight of said absorbent resin powder (A).

23. A method according to claim 22, wherein the time for completion of the reaction is the time that satisfies the following equation (b-2):

$$40 \leq \frac{(100 + R + S)}{100} \times \frac{Q}{P} \times 100 \leq 80 \quad \text{(b-2)}$$

24. A method according to claim 21, wherein said absorbent resin powder (A) is 100 parts by weight, said cross-linking agent (B) is in the range of 0.1 to 10 parts by weight, said water (C) is in the range of 0.5 to 40 parts by weight, said hydrophilic organic solvent (D) is in the range of 0 to 60 parts by weight, and said water-insoluble fine powder (E) is in the range of 0.01 to 10 parts by weight.

25. A method according to claim 24, wherein said hydrophilic organic solvent (D) is used in the range of 0.1 to 10 parts.

26. A method according to claim 24, wherein said water-insoluble fine powder (E) is used in the range of 0.01 to 5 parts by weight.

27. A method according to claim 21, wherein said cross-linking agent (B) is polyhydric alcohol compounds.

28. A method according to claim 27, wherein the time for completion of the reaction is the time that satisfies the following equation:

$$30 \leq \frac{(100 + R + S)}{100} \times \frac{Q}{P} \times 100 \leq 95 \quad \text{(b-1)}$$

wherein P is absorption capacity of absorbent resin powder (A) using physiological saline solution, Q is absorption capacity of the resultant treated absorbent resin using physiological saline solution, and R is the amount, in part by weight, of said cross-linking agent (B), and S is the amount, parts by weight, of said water-insoluble fine powder (E), based on 100 parts by weight of said absorbent resin powder (A).

29. A method according to claim 28, wherein the time for completion of the reaction is the time that satisfies the following equation (b-2):

$$40 \leq \frac{(100 + R + S)}{100} \times \frac{Q}{P} \times 100 \leq 80 \quad \text{(b-2)}$$

30. Substantially water-insoluble, absorbent, hydrogel-forming polymer, produced in accordance with the method of claim 21, 22, 27, or 28.

* * * * *